United States Patent
Le Notre et al.

(10) Patent No.: US 9,464,024 B2
(45) Date of Patent: Oct. 11, 2016

(54) PROCESS FOR THE PRODUCTION OF METHACRYLIC ACID

(71) Applicant: Stichting Dienst Landbouwkundig Onderzoek, Wageningen (NL)

(72) Inventors: Jerome Emile Lucien Le Notre, Arnhem (NL); Elinor Lindsey Scott, Amersfoort (NL); Roeland Leo Croes, Nijmegen (NL); Jacobus Van Haveren, Ede (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 14/913,833

(22) PCT Filed: Aug. 26, 2014

(86) PCT No.: PCT/NL2014/050575
§ 371 (c)(1),
(2) Date: Feb. 23, 2016

(87) PCT Pub. No.: WO2015/030580
PCT Pub. Date: Mar. 5, 2015

(65) Prior Publication Data
US 2016/0207867 A1    Jul. 21, 2016

(30) Foreign Application Priority Data
Aug. 26, 2013   (EP) .................................. 13181709

(51) Int. Cl.
*C07C 51/38*   (2006.01)

(52) U.S. Cl.
CPC .................................... *C07C 51/38* (2013.01)

(58) Field of Classification Search
CPC ...................................................... C07C 51/38
USPC ........................................................ 562/598
See application file for complete search history.

(56) References Cited

U.S. PATENT DOCUMENTS

2012/0178961 A1* 7/2012 Sanders ................... C07C 6/04
560/205

FOREIGN PATENT DOCUMENTS

WO    WO 2012069813 A1 *  5/2012  ............. C07C 51/38

OTHER PUBLICATIONS

Carlsson et al. Study of the Sequential Conversion of Citric to Itaconic to Methacrylic Acid in Near-Critical and Supercritical Water. Ind. Eng. Chem. Res., vol. 33, 1994, 1989-1996.*

* cited by examiner

*Primary Examiner* — Sikarl Witherspoon
(74) *Attorney, Agent, or Firm* — William B. Miller

(57) ABSTRACT

Disclosed is a method of making methacrylic acid, or a carboxylic derivative thereof, from itaconic acid, isomers, or precursors thereof. A starting material comprising an acid selected from the group consisting of itaconic acid, citraconic acid, mesaconic acid, citric acid, aconitic acid, isocitric acid and mixtures thereof, is subjected to contact with 0.1 eq. to 3.0 eq. of a base, at a temperature of 150° C. to 350° C., under the influence of a transition metal-containing heterogeneous catalyst. A better yield at lower temperatures is achieved.

14 Claims, No Drawings

US 9,464,024 B2

PROCESS FOR THE PRODUCTION OF METHACRYLIC ACID

CROSS-REFERENCE TO RELATED APPLICATIONS

This application is a national stage entry of International Application No. PCT/NL2014/050575, filed Aug. 26, 2014, which itself claims priority to EP Patent Application No. 13181709.0, filed Aug. 26, 2013, each of the contents of the entirety of which are incorporated by this reference.

FIELD OF THE INVENTION

The invention pertains to the synthesis of methacrylic acid (MAA), or a carboxylic derivative thereof from, itaconic acid, or a precursor or isomer thereof. Particularly, the invention pertains to a route to MAA from bio-based, non-fossil resources.

BACKGROUND OF THE INVENTION

MAA, and methyl methacrylate (MMA) are widely used in industry, mainly as monomers to make polymers having a variety of uses, such as acrylate fibers (polyMAA), cement in total hip or knee replacements (MMA), various optical glasses and lenses (PMMA). MAA can be used as a co-monomer together with MMA or ethyl acrylate to produce polymers used in coatings and slow release applications. MMA can also be used as co-monomer to produce polymers such as methyl methacrylate-butadiene-styrene (MBS). Materials can be obtained by blending PMMA with other polymers such as polyvinylchloride (PVC).

MAA is currently produced from petrochemical resources. It would be desired to find a route by which it can be produced from bio-based, renewable, non-fossil resources.

A reference relating to such a route is WO 2009/135074A2, the disclosure of which is hereby incorporated by reference. Herein a process is described by which MAA can be produced by fermentation of a renewable sugar feedstock of non-natural micro-organisms.

Another reference relating to such a route is US 2010/0035314A1, the disclosure of which is hereby incorporated by reference. Herein a process is described by which MAA can be produced by catalytic dehydration of 2-hydroxy-2-methylcarboxylic acid obtained by fermentation, of a renewable sugar feedstock of non-natural micro-organisms.

Another reference relating to such a route is the work described by Pyo et al. (Green Chem. 2012, 14, 1942), the disclosure of which is hereby incorporated by reference. Herein a process is described by which MAA can be produced by a consecutive microbial conversion and catalytic dehydration of 2-methyl-1-3-propanediol, potentially obtained by fermentation of biobased glycerol.

Another reference relating to such a route is WO 2010/058119A1, the disclosure of which is hereby incorporated by reference. Herein a process is described by which MMA can be produced by reaction of methyl propionate and formaldehyde. Methyl propionate is produced by carbonylation of ethylene in the presence of methanol where at least one of the three reactants used are obtained from biomass: ethylene by dehydration of bio-ethanol and/or carbon monoxide and methanol obtained by biobased syngas. Formaldehyde can be produced from biobased syngas.

Another reference relating to such a route is WO 2012/154450A2, the disclosure of which is hereby incorporated by reference. Herein a process is described by which MMA can be produced by successive reactions (dehydration, formaldehyde aldol condensation, esterification) starting from biobased glycols such as ethylene glycol and propylene glycol.

Another reference relating to such a route is WO 2012/089813, the disclosure of which is hereby incorporated by reference. Herein a process is described by which MAA can be produced from the decarboxylation of itaconic acid or a source thereof in the presence of base catalysts. Although this process is interesting, the yield of MAA is far below a value that would render the process of commercial interest. Whilst the yield can be increased by raising the reaction temperature, this goes with a dramatic reduction of selectivity. Also, the high temperatures per se, and the high pressures applied, make the process less interesting, if not plainly prohibitive, for economic application.

It would be desired to provide a process that allows to produce MAA in a good yield, yet with a high selectivity. Also, it would be desired to provide a process that is economically more attractive by allowing lower energy input, e.g. by requiring a lower reaction temperature, and without applied pressure.

Further, the known process is applicable to itaconic acid, its isomers. The reference mentioned that the process is also applicable to a source of these acids. However, from the disclosure itself it is clear that the actual process far making MAA is not directly applied on precursors of itaconic acid, such as citric acid. Background art on making methacrylic acid from citric acid is Carlsson et al., Ind. Eng. Chem. Res. 1994, 33, 1989. Herein a low yield, 6%, of methacrylic acid is obtained, via a dehydration reaction and two decarboxylation reactions. It would be desired to provide a process that would be directly applicable to itaconic acid precursors, particularly to citric acid, and by which methacrylic acid can be produced in better yield.

SUMMARY OF THE INVENTION

In order to address one or more of the foregoing desires, the invention, in one aspect, provides a method, of making methacrylic acid, or a salt thereof, by subjecting a starting material comprising an acid selected from the group consisting of itaconic acid, citraconic acid, mesaconic acid, citric acid, aconitic acid, isocitric acid and mixtures thereof to contact with 0.1 eq. to 3.0 eq. of a base, at a temperature of 150° C. to 350° C., under the influence of a transition metal-containing catalyst.

In another aspect, the invention pertains to the use of a transition metal catalyst for the purpose of increasing the yield and selectivity of the synthesis of methacrylic acid, or a salt thereof, from a starting material comprising an acid selected from the group consisting of itaconic acid, citraconic acid, mesaconic acid, citric acid, isocitric acid, aconitic acid, and mixtures thereof.

DETAILED DESCRIPTION OF THE INVENTION

In a broad sense, the invention is based on the judicious insight to add a transition metal catalyst to the base-catalyzed process of decarboxylating itaconic acid or a precursor or isomer thereof. The use of the catalyst allows to obtain a dramatic increase in yield and/or selectivity, in a reaction conducted under much milder conditions than available in the art. Also, the use of the catalyst in accordance with the invention allows a feasible process to produce methacrylic acid from citric acid, isocitric acid, itaconic acid, citraconic acid, mesaconic acid, aconitic acid, and mixtures thereof. Therewith, the invention provides a process wherein citric acid, and preferably a bio-based source thereof, can be itself used, as a starting material for the direct synthesis of the valuable chemical methacrylic acid. In addition to producing methacrylic acid, the process of the invention also allows the direct production of salts of methacrylic acid, with the base forming the counterion of the salt. Further carboxylic derivatives, such, as esters, can be produced by converting the acid or salt through known methods, such as esterification.

The invention will now be discussed in more detail with reference to the starting materials, the process conditions, and the catalysts involved.

To start with the latter, the transition metal catalysts can be of the homogeneous or heterogeneous type.

In the process of the invention, the reactants are in a liquid phase, i.e. a solution or suspension of the starting material in an aqueous base, such as sodium hydroxide solution. In the event of homogeneous catalysis, the catalyst will be in the same phase as the reactants. This typically holds for solutions of salts of transition metals.

In catalysts of the heterogeneous type, the phase of the catalyst differs from that of t he reactants. In the case of heterogeneous catalysis, the catalyst will generally be in a solid phase, and will preferably be present in the form of particles. This may refer to catalyst systems of both the fluidized bed and the fixed bed types.

Although the catalyst can be identical to the metal itself, it is preferred for the transition metal to be provided on a support. Supported catalysts are well-known to the skilled person. Typical supports include metal oxides, silica, and carbon.

The metal oxide support generally is a catalyst support, made of at least one oxide of a main group or transition metal or metalloid, including compounds which comprise more than one metal and/or metalloid. Preference is given in this connection to oxides of metals or metalloids of main group 2 of the Periodic Table, such as MgO, CaO or BaO, oxides of metals or metalloids of main group 3 of the Periodic Table, such as $Al_2O_2$ or lanthanide oxides or oxides of metals or metalloids of main group 4 (IVA or IVB) of the Periodic Table, such as $TiO_2$, $ZrO_2$, $SnO_2$, or $SiO_2$. Also $Fe_2O_2$ can be employed. The compounds having more than one metal and/or metalloid are preferably silicates, especially aluminosilicates.

Carbon supports are, e.g., activated carbons, carbon blacks, graphites, carbon nanotubes, carbon nanofibers, etc.

The support is preferably selected from the group consisting of alumina, carbon, barium sulfate, and silica. Alumina and carbon supports are most preferred.

The catalyst will generally comprise, in weight percentages relative to the support, of from 0.1 wt % to 65 wt % of the transition metal, preferably 1-20 wt %, and more preferably 5 to 10 wt. %, As the skilled person knows, the preferred metal loading can differ per metal (e.g., nickel being preferred at the high end of the above range, particularly 65 wt. %). The supported transition metal catalyst is preferably employed in the form of a powder or granules. The catalyst is present in the process so as to preferably provide an amount of 0.1 mole % to 2.5 mole % of the transition metal, calculated, on the starting material.

The transition metal can be as the element itself or in the form of a salt with an oxidation state, of 1, 2, or 3 of an inorganic or organic acid such as halides, oxides, acetates, or hydroxides, e.g. palladium hydroxide. Suitable salts for homogeneous catalysis include $PdCl_2$, $PdBr_2$, $PdI_2$, $Pd(OAc)_2$, $Pd(CN)_2$, PdO, $PtCl_2$, $PtBr_2$, $PtI_2$, $PtCl_4$, $PtO_2$, $RuCl_3$, $RuI_3$, $RuO_2$, $RuO_4$, $NiCl_2$, $NiBr_2$, $NiI_2$, $NiF_2$, $Ni(OH)_2$, $Ni(OAc)_2$, $Ni(CO)_4$, AuCl, $AuCl_3$, AuBr, $Au_2O_3$, $RhCl_3$, $RhBr_3$, $RhI_3$, and $Rh_2O_3$.

Heterogeneous catalysts are preferred. Therewith a process advantage can be attained, in the sense that separation of catalysts and products is easier. Also, heterogeneous catalysts have an advantage in that they are better recyclable.

Preferably, the transition metal is provided as the element itself, i.e. it is in the metallic form.

Transition metals are the metals in the deblock of the periodic table of elements, which comprises groups 3 to 12. Preferably, the transition metal catalysts used in the invention are in accordance with a more narrow definition thereof, viz. those elements that, have partly filled d suitable either in the neutral atom or in ions in common oxidation states. Thus, preferred transition metals are those of groups 3-11 of the periodic table. More preferably, the transition metal comprised in the catalyst is selected from the elements of groups 6, 7, 8, 10, and 11 of the periodic 25 table, with groups 10 and 11 more preferred, and group 10 most preferred.

By another preference, the transition metal comprised in the catalyst is selected from, the group consisting of ruthenium, rhodium, nickel, palladium, platinum, gold, and tungsten.

The transition metal can be present as a single species, or as a mixture of two or more transition metals.

The method of the invention involves a decarboxylation reaction, conducted at elevated temperature. In the prior art process described above, the temperature ranges from 250° C. to 350° C., and high pressures are applied, typically 200 bar. In the method of the invention, both the temperature and the pressure can be advantageously lower. The lower pressure is a process advantage, but the pressure itself is not believed to be particularly critical, provided that, at the reaction temperature, the pressure is sufficiently high for the reactants to be in a liquid state. Typical pressures range from 10 bar to 100 bar. Particularly, in the method of the invention pressure is not applied. By conducting the reaction in a pressure vessel, the only pressure is that, which builds up during the reaction. This pressure will be of the order of 20 to 50 bar, preferably 40 bar. Thus, in a preferred embodiment, the method of the invention is conducted in a pressure vessel without pressure applied.

The reaction temperature is generally in. a. range of from 150° C. to 350° C. Preferably, in order to obtain both a good yield and selectivity, and additionally avoid the energy disadvantages associated with the high temperatures used in the art, the temperature set in the method of the invention is preferably in a range of from 200° C. to 300° C.

It will be understood by the skilled person that for each catalyst system an optimum exist for the reaction temperature. As further guidance in this respect, it is preferred that in the event of a catalyst, or mixture of catalysts, selected from the elements in groups 6, 7, 8, 9, 10. and 11 of the Periodic Table of Elements, and particularly for rhodium, nickel palladium, platinum, gold, and tungsten, the temperature preferably is in a range of from 225° C. to 275° C. In the event that the transition metal is ruthenium, the temperature is preferably in a range of from 200° C. to 225° C.

The decarboxylation method of the invention, conducted under catalysis by a transition metal, is essentially a base-catalyzed process. Suitable bases are described in WO 2012/069813. As cited therein, the catalyst preferably comprises a source of OH ions. Preferably, the base catalyst comprises a metal oxide, hydroxide, carbonate, acetate (ethanoate), alkoxide, hydrogen carbonate or salt of a decomposable di- or tri-carboxylic acid, or a quaternary ammonium compound of one of the above; more preferably a Group I or Group II metal oxide, hydroxide, carbonate, acetate, alkoxide, hydrogen carbonate or salt of a di- or tri-carboxylic acid or methacrylic acid. The base catalyst may also comprise one or more amines. Preferably, the base catalyst is selected from NaOH, KOH, $Mg(OH)_2$, $Ca(OH)_2$, and mixtures thereof. Express reference is hereby made to other suitable bases, as discussed in WO 2012/069813.

The base catalyst may be homogeneous or heterogeneous. In one embodiment, the catalyst may be dissolved in a liquid reaction phase. However, the catalyst may be suspended on a solid support over which the reaction phase may pass. In this scenario, the reaction phase is preferably maintained in a liquid, more preferably, an aqueous phase. In the alternative, the base catalyst is a homogeneous catalyst, the base being present as an aqueous solution, with the starting material for the reaction being dissolved in the same medium.

The amount of the base is in a. range of 0.1 eq. to 3.0 eq., preferably 0.5 eq. to 2 eq., more preferably 0.8 eq. to 1.2 eq., and most preferably about one equivalent (1 eq.). E.g., in the case of itaconic acid as the starting material and NaOH. as the base, the NaOH will be present preferably generally in an amount of 0.05 M to 0.3 M, more preferably 0.1 M to 0.2 M, and most preferably 0.15 M (1 eq.).

The starting materials used in the invention comprise an acid selected from the group consisting of itaconic acid, citraconic acid, mesaconic acid, (iso)citric acid, aconitic acid and mixtures thereof. Thus, the invention can be applied to itaconic acid, the isomers of itaconic acid (which are citraconic acid and mesaconic acid) and the main precursor of itaconic acid, which is citric acid, as well as the dehydrated product thereof, viz. aconitic acid. The method, of the invention can be applied to the acids themselves, either alone or in combination, or to a starting material comprising these acids. The latter is particularly preferred for using the method, of the invention m order to obtain value from bio-based sources of citric acid. The main sources of interest for use in the invention are from broths of carbohydrate fermentation processes to citric acid, isocitric acid, itaconic acid, citraconic acid, mesaconic acid, aconitic acid and mixtures thereof, that can be used directly or after filtering of cells; streams and side streams of the agro-food industry including molasses, raw (sugar) juice, vinasse, bagasse, protamylasse, etc.; and liquids obtained from fruits and vegetables, especially citrus fruits.

The method of the invention compares favorably to the state of the art, in respect of both the synthesis of methacrylic acid from itaconic acid and isomers (see WO 2012/069813) and the synthesis of methacrylic acid from citric acid, as reported reported by Carlsson et al., mentioned above. E.g. even without specific optimization a yield of 35% can be obtained, where the reaction scheme of Carlsson results in only 6%.

The invention also pertains to the use of a transition metal heterogeneous catalyst for the purpose of increasing the yield and selectivity of the synthesis of methacrylic acid, or a carboxylic derivative thereof, from a starting material comprising an acid selected, from the group consisting of itaconic acid, citraconic acid, mesaconic acid, citric acid, aconitic acid and mixtures thereof. This use, which, embodies a purpose of the catalysts mentioned not hitherto described in the art, can be applied in practice by conducting a method of making methacrylic acid in accordance with the various embodiments described above.

The method of the invention can also be applied in a through synthesis to polymers of methacrylic acid or esters thereof. This method comprises making methacrylic acid in accordance with the method substantially described hereinbefore, optionally esterifying the methacrylic acid obtained, and subjecting the methacrylic acid or ester thereof to polymerization in a manner generally known to t be skilled person.

All in all, very favorable results are obtained with the method of the invention. These results can be acknowledged with reference to the process advantages of a lower temperature and the absence of applied pressure. These results can further be acknowledged with reference to higher yield of methacrylic acid, and to a better by-products profile.

The invention will be illustrated hereinafter with reference to the following non-limiting examples.

EXAMPLE 1

Base-catalyzed decarboxylation of itaconic acid (400 mg, 3.0 mmol), with and without transition metal catalyst Pd/C (2.5 mol %). Base is 0.15 M NaOH (20 mL). Reaction temperature is 250° C. Pressure (not applied, solely as built up in reaction vessel) is 40 bar. Reaction time is 1 hour. The results are summarized in Table 1. The conversion (Conv.) refers to the percentage of itaconic acid that has been converted, to anything, as a result of the process. The yield of methacrylic acid (MAA) is the mole percentage of MAA retrieved in the product composition. Other mole % included are specified for the isomers (mesaconic acid and citraconic acid formed in the reaction), erotonic and pyruvic acid by-products, and unspecified by-products ("others").

TABLE 1

| Metal catalyst | Conv. (%) | MAA (mol %) | By-products (mol %) | | | |
|---|---|---|---|---|---|---|
| | | | Isomers | Crotonic | Pyruvic | Others |
| none | 96.4 | 31.6 | 12.4 | 0.2 | 1.1 | 51.2 |
| Pd/C | 97.3 | 64.6 | 11.0 | 0.2 | 3.3 | 18.2 |

The method of the invention leads, at the same conversion to a higher yield. The method also leads to a narrower distribution of by-products.

EXAMPLE 2

The same procedure and conditions as in Example 1 is applied to a variety of catalysts, as well as in the absence of catalysts.

The results are given in Table 2, wherein the percentages are identified of:

Itaconic acid (starting material)

Isomers of itaconic acid

Methacrylic acid (MAA)

Other products

The reaction conditions being equal for all catalysts, they do not necessarily represent the optimum. For two catalysts, a variation was made by changing the temperature (temperatures indicated in the table).

TABLE 2

| Catalyst | Conv. (%) | Itaconic acid (mol %) | Isomers (mol %) | MAA (mol %) | Others (mol %) |
|---|---|---|---|---|---|
| None | 96.4 | 3.6 | 12.4 | 31.6 | 52.4 |
| Activated C | 96.1 | 3.9 | 10.8 | 30.7 | 54.6 |
| $Al_2O_3$ | 96.4 | 3.6 | 8.3 | 38.5 | 49.6 |
| Pd/C | 97.3 | 2.7 | 11.3 | 64.6 | 21.4 |
| Pd/$Al_2O_3$ | 96.4 | 3.6 | 13.5 | 58.1 | 24.8 |
| Pd(OH)$_2$/C | 95.1 | 4.9 | 18.4 | 56.6 | 20.1 |
| Pd/BaSO$_4$ | 95.5 | 4.5 | 16.6 | 65.2 | 13.7 |
| Pt/C | 95.9 | 4.1 | 16.3 | 47.0 | 32.6 |
| Pt/$Al_2O_3$ | 96.1 | 3.9 | 15.7 | 67.8 | 12.6 |
| Pt/$Al_2O_3$ (225° C.) | 92.1 | 7.9 | 28.7 | 27.8 | 35.6 |
| Pt/$Al_2O_3$ (275° C.) | 99.0 | 1.0 | 2.7 | 23.8 | 72.5 |
| Ru/C | 99.0 | 1.0 | 1.7 | 3.5 | 93.8 |
| Ru/C (200° C.) | 90.9 | 9.1 | 26.7 | 23.4 | 40.8 |
| Ru/C (225° C.) | 98.3 | 1.7 | 1.3 | 24.6 | 72.4 |
| Ni/SiO$_2$ | 95.9 | 4.1 | 15.8 | 57.5 | 22.6 |
| Au/C | 97.3 | 2.7 | 9.7 | 62.7 | 24.9 |
| Rh/C | 98.0 | 2.0 | 7.1 | 46.0 | 44.9 |

EXAMPLE 3

Using a platinum on alumina (Pt/$Al_2O_3$) catalyst, and the conditions identified in Example 1, citric acid was subjected to the method of the invention. The results are indicated in Table 3, m comparison with those reported by Carlsson et al., Ind. Eng. Chem. Res. 1994, 33, 1989.

TABLE 3

| Process | Conv. (%) | MAA (mol %) | By-products (mol %) | | | |
|---|---|---|---|---|---|---|
| | | | Itaconic | Mesaconic | Citraconic | Others |
| Carlsson | 100 | 6 | 35.0 | 16.0 | 25.0 | 18.0 |
| Invention | 99.6 | 34.5 | 4.0 | 10.5 | 4.5 | 46.1 |

The invention claimed is:

1. A method of making methacrylic acid, or a salt thereof, by subjecting a starting material comprising an acid selected from the group consisting of itaconic acid, citraconic acid, mesaconic acid, citric acid, aconitic acid, isocitric acid and mixtures thereof, to contact with 0.1 eq. to 3.0 eq. of a base, at a temperature of 150° C. to 350° C., under the influence of a transition metal-containing catalyst.

2. A method according to claim 1, wherein the catalyst is a heterogeneous catalyst.

3. A method according to claim 2, wherein the catalyst comprises a transition metal in a metallic or salt form carried by a support.

4. A method according to claim 3, wherein the support is selected from the group consisting of alumina, carbon, barium sulfate, and silica.

5. A method according to claim 1 or claim 3, wherein a transition metal is present in the metallic form.

6. A method according to claim 1, wherein the transition metal-containing catalyst includes one or more elements from groups 6, 7, 8, 9, 10, and 11 of the Periodic Table of Elements.

7. A method according to claim 6, wherein the transition metal is selected from the group consisting of rhodium, nickel, palladium, platinum, gold, and tungsten.

8. A method according to any one of claim 1, claim 3 or claim 6, wherein the temperature is in a range of from 200° C. to 300° C.

9. A method according to claim 8, wherein the temperature is in a range of from 225° C. to 275° C.

10. A method according to claim 9, wherein the transition metal of the transition metal-containing catalyst is ruthenium, and the temperature is in a range of from 200° C. to 225° C.

11. A method according to claim 1, wherein the base is present in a range of from 0.8 eq. to 1.2 eq., preferably 1 eq.

12. A method according to claim 1, conducted in a pressure vessel without pressure applied.

13. A method according to claim 1, wherein the starting material is a crude liquid selected from the group consisting of broths resulting from carbohydrate fermentation, liquid streams obtained as a main stream or a side streams from the agro-food industry, wherein the acid is directly converted to methacrylic acid from the crude liquid.

14. A method according to claim 1 or claim 3, wherein the transition metal is in a salt form.

* * * * *